United States Patent
Chai

(10) Patent No.: US 11,684,564 B2
(45) Date of Patent: Jun. 27, 2023

(54) COSMETIC COMPOSITION FOR IMPROVING SKIN CONTAINING TARAXACUM COREANUM PHYTOPLACENTA CULTURE EXTRACT THAT HAS MOISTURIZING AND SOOTHING EFFECTS FOR EXTREMELY DRY SKIN SUCH AS ATOPIC DERMATITIS, AND SKIN BARRIER STRENGTHENING EFFECT

(71) Applicant: TALITHAKOUM CO., LTD., Seoul (KR)

(72) Inventor: Moon Sun Chai, Seoul (KR)

(73) Assignee: TALITHAKOUM CO., LTD., Seoul (KR)

( * ) Notice: Subject to any disclaimer, the term of this patent is extended or adjusted under 35 U.S.C. 154(b) by 0 days.

(21) Appl. No.: 17/372,618

(22) Filed: Jul. 12, 2021

(65) Prior Publication Data

US 2022/0008328 A1    Jan. 13, 2022

(30) Foreign Application Priority Data

Jul. 13, 2020   (KR) .................. 10-2020-0086211

(51) Int. Cl.
| | | |
|---|---|---|
| *A61K 8/9789* | (2017.01) | |
| *A61Q 17/00* | (2006.01) | |
| *A61Q 17/04* | (2006.01) | |
| *A61Q 19/00* | (2006.01) | |
| *A61Q 19/08* | (2006.01) | |
| *C12N 5/04* | (2006.01) | |

(52) U.S. Cl.
CPC ............ *A61K 8/9789* (2017.08); *A61Q 17/00* (2013.01); *A61Q 17/04* (2013.01); *A61Q 19/007* (2013.01); *A61Q 19/08* (2013.01); *C12N 5/04* (2013.01)

(58) Field of Classification Search
None
See application file for complete search history.

(56) References Cited

U.S. PATENT DOCUMENTS

2016/0058696 A1*  3/2016  Kim ................. A61K 36/28
                                                  435/41

FOREIGN PATENT DOCUMENTS

| CN | 105582036 A | 5/2016 |
| KR | 1020150039187 A | 4/2015 |
| KR | 1020160049886 A | 5/2016 |
| KR | 1020150104754 A | 8/2016 |

OTHER PUBLICATIONS

Database wINCHI—New Online Internal,Taraxacum Coreanum Phytoplacenta Culture Extract (2020).
Im et al., "Nitric Oxide Production Inhibitory and Scavenging Activity and Tyrosinase Inhibitory Activity of Extracts from Taraxaxum officinale and Taraxacum coreanum," Korean Journal of Medicinal Crop Science. 19(5): 362-267 (2011).
Announcement of the results of the 9th Ingredient Name Standardization Committee in 2020. Korea Cosmetic Association. May 5, 2020. https://kcia.or.kr/cid/cs/notice.php?type=view&no=12831&ss=page%3D4%26skind%3D%26sword%3D%26ob%3D.
Derma Cosmetic. Cosmetics Beauty Media Course in Korea. Jun. 9, 2017. https://www.cosinkorea.com/news/article.html?no=20247.
Lee et al., "Biological Activities of the Water Extract and its Fractions from Taraxacum coreanum Nakai" Kor. J. Pharmacogn. 42(2) :195-200 (2011).
"[Oriental Medicine Promotion Foundation's Story of Herbal Medicine—Dandelion] Lowers fever and detoxifies . . . It is also used to improve oncology and gastritis," Apr. 3, 2018. https://www.yeongnam.com/web/view.php?key=20180403.010220751270001.

* cited by examiner

*Primary Examiner* — Nannette Holloman
(74) *Attorney, Agent, or Firm* — Raphael Bellum PLLC

(57) ABSTRACT

The present disclosure relates to a Taraxacum Coreanum phytoplacenta cell culture extract that has moisturizing and soothing effects for extremely dry skin such as atopic dermatitis, and skin barrier strengthening effect. The Taraxacum Coreanum phytoplacenta cell culture or an extract thereof according to the present disclosure is non-toxic to skin cells, and has an efficacy of moisturizing, anti-aging, strengthening the skin barrier, improving wrinkles, soothing the skin, protecting the skin from UV rays, and protecting the skin from blue light, etc.

17 Claims, No Drawings

COSMETIC COMPOSITION FOR IMPROVING SKIN CONTAINING TARAXACUM COREANUM PHYTOPLACENTA CULTURE EXTRACT THAT HAS MOISTURIZING AND SOOTHING EFFECTS FOR EXTREMELY DRY SKIN SUCH AS ATOPIC DERMATITIS, AND SKIN BARRIER STRENGTHENING EFFECT

TECHNICAL FIELD

The present disclosure relates to a cosmetic composition for improving skin containing a Taraxacum Coreanum phytoplacenta culture extract that has moisturizing and soothing effects for extremely dry skin such as atopic dermatitis, and skin barrier strengthening effect.

BACKGROUND ART

Human skin undergoes changes due to various internal and external factors by growing older. Internally, the secretion of various hormones that control the metabolism is reduced, and the function of immune cells and the activity of cells are lowered, so that the biosynthesis of the constituent proteins necessary for the living body is reduced. Due to the destruction of the ozone layer, the content of ultraviolet rays of the sun reaching the earth surface increases, and free radicals and active harmful oxygen increase as environmental pollution further intensifies. Therefore, various changes are caused externally, such as a decrease in the skin thickness, an increase in wrinkles, and a decrease in elasticity as well as a frequent occurrence of skin troubles.

If skin aging progresses, a decrease in the division of keratinocytes and fibroblasts, a decrease in collagen synthesis, an increase in MMP production, an increase in the signal transduction of melanin production, etc., occur, and thereby wrinkles will increase with a reduction of the skin elasticity, and spots, freckles, and age spots will increase. In particular, around the age of 40, the balance of hormones is disrupted, and the cell regeneration ability, collagen synthesis ability, and moisture content of the stratum corneum, which is important for skin moisturizing, are significantly lowered. The reason for the significant decrease in moisture content is suggested as a decrease in the lipid component of the stratum corneum and a decrease in natural moisturizing factors. Eventually, aging skin lacks the amount of moisture supplied from the lower epidermis to the stratum corneum, resulting in severe skin dryness, which leads to be prone to inflammation and pruritus. On the other hand, wrinkles in the skin are caused by an imbalance in the synthesis and decomposition of collagen, and usually, in the skin, the synthesis of type I collagen is in balance with its decomposing enzyme, MMP-1. However, in photoaging skin, the synthesis of type I and III collagen is lowered and the activity of MMP-1 is increased. These matrix metalloproteinases (MMPs) are proteolytic enzymes that decompose the extracellular matrix and are known to be involved in wound healing or tissue regeneration in normal conditions.

There changes lead to an increase in interest in materials that can inhibit skin aging and social demand for cosmetics containing the above materials, and the development of materials that are biocompatible and have excellent skin penetration rate is emerging as an important task. Recently, various methods have been applied, and among them, various vegetable resources and peptides have been studied to recover the skin damage as described above.

'Callus' is a wound-healing tissue that enlarges and closes the wound by restoring cell division ability when a plant is injured, and refers to a lump of special tissue produced by culturing the tissue cut from the plant in a medium containing auxin, etc. Recently, interest in the use of such callus has been heightened, and research is being conducted in various fields. Plants have excellent totipotency, in which entire individuals are re-formed even when only a part of the plant, such as leaves, stems, and roots, is transplanted. Callus is characterized in that it can be induced from any part of a plant through plant cell culture, especially tissue culture, and can be continuously produced by subculture. The basic principle of culturing plant cells uses the biological fact that every plant cell has the ability to build the entire plant from which it originates. This totipotency is comparable to the pluripotency of embryonic stem cells in animals. Therefore, it is acceptable that plant cells have a positive effect on the protection and activation of skin stem cells. On the other hand, the 'placenta' of a plant, like the placenta derived from animals, is an important part that controls seed development, and is the part to which ovary attaches within the ovary of pistil. Differentiation of the ovule is impossible without a placenta, and the placenta contains more phytochemicals, which are physiologically active nutrients, than other tissues. The placenta is involved in the maintenance of homeostasis against external stimuli, and structural maintenance proteins such as chaperones are distributed therein.

If callus culture, which is an undifferentiated cell mass through tissue culture using the properties of these plants, is used, it can be considered as valuable as a cosmetic raw material with excellent physiological activity.

DISCLOSURE

Technical Problem

The object of the present disclosure is to solve the above problems and other problems related thereto.

An exemplary object of the present disclosure is to provide a method for preparing a cosmetic composition containing a phytoplacenta cell culture of Taraxacum Coreanum or an extract of the culture.

Another exemplary object of the present disclosure is to provide a cosmetic composition for moisturizing the skin containing a phytoplacenta cell culture of Taraxacum Coreanum or an extract of the culture according to the above method.

Another exemplary object of the present disclosure is to provide a cosmetic composition for strengthening the skin barrier containing a phytoplacenta cell culture of Taraxacum Coreanum or an extract of the culture according to the above method.

Another exemplary object of the present disclosure is to provide a cosmetic composition for protecting the skin from an ultraviolet containing a phytoplacenta cell culture of Taraxacum Coreanum or an extract of the culture according to the above method.

Another exemplary object of the present disclosure is to provide a cosmetic composition for protecting the skin from blue light containing a phytoplacenta cell culture of Taraxacum Coreanum or an extract of the culture according to the above method.

Another exemplary object of the present disclosure is to provide a cosmetic composition for preventing or alleviating skin stress containing a phytoplacenta cell culture of Taraxacum Coreanum or an extract of the culture according to the above method.

Another exemplary object of the present disclosure is to provide a cosmetic composition for protecting the skin from a fine dust containing a phytoplacenta cell culture of Taraxacum Coreanum or an extract of the culture according to the above method.

Another exemplary object of the present disclosure is to provide a cosmetic composition for soothing the skin containing a phytoplacenta cell culture of Taraxacum Coreanum or an extract of the culture according to the above method.

The technical challenge to be achieved according to the technical idea disclosed in the present specification is not limited to the challenge for solving the above-mentioned problems, and another challenge not mentioned above can be clearly understood by those skilled in the art from the following description.

Technical Solution

This will be described in detail as follows. Meanwhile, each description and embodiment disclosed in the present application may be applied to another each description and embodiment. That is, all combinations of the various elements disclosed in the present application fall within the scope of the present application. In addition, it cannot be seen that the scope of the present application is limited by the specific descriptions described below.

One aspect of the present disclosure for achieving the above object provides a method for preparing a cosmetic composition containing a phytoplacenta cell culture of Taraxacum Coreanum or an extract of the phytoplacenta cell culture, the method including: (a) separating and culturing phytoplacenta cells from the phytoplacental tissue in ovary of Taraxacum Coreanum plant; and (b) preparing a composition containing the culture obtained in the step (a) or an extract of the phytoplacenta cell culture.

In one aspect, the present disclosure relates to a composition for external skin application for improving the skin, containing the Taraxacum Coreanum phytoplacenta cell culture or an extract thereof according to the method above, as an active ingredient. Specifically, the phytoplacenta cell culture or an extract thereof may be contained in an amount of 0.1 to 10% by weight based on the total weight of the composition. Such a ratio is only a preferable range, and for example, in the following examples, it was confirmed that it had excellent efficacy by testing at 1%, 5% and 10% concentrations, and cell viability was also not affected even at 10%. In addition, even in the case of 20% or 30% or more, it is obvious to those skilled in the art that it has excellent skin improvement effect, skin barrier strengthening, skin improvement, skin moisturizing, skin anti-aging, skin wrinkle improvement, skin protection from ultraviolet or blue light, protection from skin stress, skin soothing and a fine dust blocking function, etc.

A method for preparing a cosmetic composition containing a Taraxacum Coreanum phytoplacenta cell culture or an extract thereof according to the present disclosure comprises the following steps:

(a) separating and culturing phytoplacenta cells from the phytoplacenta tissue in ovary of Taraxacum Coreanum plant; and (b) preparing a composition containing the culture obtained in the step (a) or an extract thereof.

In the present disclosure, the step (b) may include a step of preparing a composition by drying, pulverizing, and mixing the phytoplacenta cell culture of Taraxacum Coreanum plant obtained in the step (a) with purified water.

In the present disclosure, the step (b) may include a step of preparing the composition by drying, pulverizing and mixing the phytoplacenta cell culture of Taraxacum Coreanum plant obtained in the step (a) with purified water and then performing extraction under the reduced pressure, ultrasonic extraction or hot water extraction.

In the present disclosure, the Taraxacum Coreanum phytoplacenta cell culture (cultured product) itself is used, or the culture is filtered and used, or the culture is disrupted and used, or the culture is dried and powdered, and then the obtained powder may be used by dissolving it in purified water.

An "extract" herein refers to an extract obtained by powdering the phytoplacenta cell culture of Taraxacum Coreanum plant, or by various conventionally known extraction methods such as extraction method under a reduced pressure, a cold water extraction method, a hot water extraction method, and an ethanol extraction method, etc.

The extraction method in the present disclosure is not particularly limited, and examples thereof include extraction under a reduced pressure, cold water extraction, ultrasonic extraction, reflux extraction, hot water extraction, etc.

Here, the extraction under a reduced pressure may be a low-temperature extraction under a reduced pressure, and for example, the phytoplacenta cell culture of Taraxacum Coreanum plant may be extracted under a reduced pressure at a low temperature (60° C. to 80° C.) for 6 to 8 hours. In addition, there is no restriction on the extraction device specially used for extraction under a reduced pressure, and upon extraction under a reduced pressure, the extract having excellent effect as a cosmetic composition material of the present disclosure is obtained by performing the extraction under a reduced pressure at a pressure of 0.03 to 0.3 MPa, specifically, at a pressure of 0.05 to 0.1 MPa.

Here, in the case of the hot water extraction, the hot water extract is obtained by heating at 80 to 100° C. for 8 to 48 hours in a hot water distiller.

In the case of the cold water extraction, for example, the phytoplacenta tissue culture itself or a dried powder thereof is mixed with cold water (15 to 25° C.) and extracted for 3 days to obtain a cold water extract.

Alternatively, the extract may be prepared by performing the extraction using water, an organic solvent, or a mixed solvent thereof. The extracted liquid may be used directly or used by performing the concentration and/or dryness. In case of the extraction using an organic solvent, methanol, ethanol, isopropanol, butanol, ethylene, acetone, hexane, ether, chloroform, ethyl acetate, butyl acetate, dichloromethane, N,N-dimethylformamide (DMF), dimethyl sulfoxide (DMSO), 1,3-butylene glycol, propylene glycol, or an organic solvent as a mixture thereof is used, and the extraction may be carried out at room temperature or by warming the temperature under conditions in which the active ingredient of the herbal medicine is not destroyed or its destruction is minimized. Depending on the organic solvent for an extraction, the degree of extraction and loss of the active ingredient of the drug may be different, so that an appropriate organic solvent may be selected and used.

In the present disclosure, the extract may be used by concentration or dilution, and a distillate of the extract may be used.

In the present disclosure, anti-aging is a concept including skin protection and skin condition improvement, skin whitening, prevention or improvement of skin aging and wrinkles, pore shrinkage, tightening, skin protection and alleviation of inflammatory response of the skin, an ability for improving immune disease, or an improvement of skin barrier function, skin irritation relief, skin cell proliferation and regeneration ability, antioxidant activity, and an ability of enhancing collagen synthesis.

In the present disclosure, the meaning of "contained as an active ingredient" is to contain an effective amount to represent the desired effect in the present disclosure, such as skin moisturizing, an improvement of skin barrier strengthening, wrinkle improvement, etc., as a skin cosmetic composition.

In the skin barrier protection function according to the present disclosure, a skin barrier refers to the stratum corneum, which is the outermost layer of the epidermis, and is mainly composed of non-nucleated flat corneocytes. A multi-lamellar lipid layer formed of intercellular lipids such as ceramide, cholesterol, and fatty acids synthesized by keratinocytes of the skin barrier maintained through the division and differentiation process of normal epidermal cells play a role as a protective layer to prevent moisture in the skin from evaporating. Meanwhile, among these intercellular lipids, omega hydroxy ceramide is chemically covalently linked with involucrin, a protein of the outer layer of corneocytes, to form a corneocyte lipid envelope (CLE), thereby playing a role in physically stabilizing intercellular lipids in the form of a multi-layered lipid layer and strengthening the barrier function.

The composition according to the present disclosure is delivered to the stratum corneum through skin application to promote the differentiation of keratinocytes, and thus has an effect of improving the thickness of the epidermal layer to be thick, and has an excellent effect of restoring the skin barrier damage, and may be usefully used for the treatment and prevention of skin diseases induced by damage to the skin barrier. Skin diseases caused by damage to the skin barrier include, but are not limited to, atopic dermatitis, xeroderma, psoriasis, ichthyosis, and acne, etc.

In addition, the skin barrier protection mechanism was confirmed by increasing the amount of proteins, occludin and claudin-1, which are proteins constituting tight junctions. Filaggrin is one of several structural proteins expressed by keratinocytes in the differentiation stage, and is involved in differentiation from the basal layer of the epidermis to the stratum corneum, and is also used as a major indicator of skin moisture retention and skin membrane function as natural moisture factor (NMF) essential for skin moisture retention, and the phytoplacenta cell culture according to the present disclosure has excellent skin barrier protection, strengthening, and improvement functions as the gene expression of filaggrin is significantly increased.

In addition, it was confirmed that the phytoplacenta cell culture according to the present disclosure has superior skin cell protection effect according to ultraviolet irradiation or blue light irradiation. Thus, the phytoplacenta cell culture may be used for skin protection according to ultraviolet irradiation.

On the other hand, like the placenta derived from animals, placenta of a plant is an important part that controls seed development, and is the part to which the ovary attaches within the ovary of the pistil. Usually, the placenta is usually located at the edge of the carpel forming the ovary, sometimes also in the middle vein of the carpel. Also, the placenta is sometimes formed in the form of a column at the base of the ovary or upright in the ovary from the base.

In this respect, the present disclosure relates to a method for preparing a cosmetic composition containing the phytoplacenta cell culture of Taraxacum Coreanum plant or an extract thereof, including the steps of (a) isolating and culturing the phytoplacenta tissue of Taraxacum Coreanum plant; and (b) preparing a composition containing the phytoplacenta cell culture of Taraxacum Coreanum or an extract thereof.

In the step (a), specifically, an appropriate medium may be selected for culturing the phytoplacenta cells of Taraxacum Coreanum. If there is a medium generally used for plant tissue culture in the technical field, it is available without limitation. In plants, MS medium, B5 medium, etc., are mainly used, and for example, the composition of MS medium (based on 1 L) may be $CoCl_2 \cdot 6H_2O$ 0.025 mg, $CuSO_4 \cdot 5H_2O$ 0.025 mg, FeNaEDTA 36.70 mg, $H_3BO_3$ 6.20 mg, KI 0.83 mg, $MnSO_4 \cdot H_2O$ 16.90 mg, $Na_2MoO_4 \cdot 2H_2O$ 0.25 mg, $ZnSO_4 \cdot 7H_2O$ 8.60 mg, $CaCl_2$ 332.02 mg, $KH_2PO_4$ 170.00 mg, $KNO_3$ 190.00 mg, $MgSO_4$ 180.54 mg, $NH_4NO_3$ 1650.00 mg.

In addition, minositol, thiamine, zeatin, and sucrose may be included in the medium, and through a combination of these materials, an excellent yield of inducing the phytoplacenta cell of Taraxacum Coreanum may be achieved. In the present disclosure, thiamine and zeatin may be included in a weight ratio of 2 to 6:1. As an example, 100 mg of minositol, 0.4 mg of thiamine, 0.1 mg of zeatin, and 30 g of sucrose in MS medium (based on 1 L) may be included.

In the present disclosure, in the step (b), the composition containing the phytoplacenta cell culture of Taraxacum Coreanum obtained through the culturing in step (a) as it may be prepared as an external composition for the skin in an appropriate form, or may be prepared into a cosmetic composition in an appropriate form by obtaining it in the form of an extract through a known extraction method.

For example, in the step (b), the phytoplacenta cell culture of Taraxacum Coreanum obtained in step (a) is dried, pulverized and mixed with purified water to prepare a composition, or the phytoplacenta cell culture of Taraxacum Coreanum obtained in step (a) is dried, pulverized and mixed with purified water, and then is subject to cold water extraction, hot water extraction, or ethanol extraction to prepare a composition.

As another example, the culture obtained in step (a) may be prepared by powdering it after drying with hot air to evaporate moisture.

The cosmetic composition may contain a carrier acceptable in the cosmetic formulation. Here, the phrase "carrier acceptable in cosmetic formulation" refers to compounds or compositions that are already known and used, that may be included in cosmetic formulation, or compounds or compositions to be developed in the future that have no toxicity, instability, or irritation beyond what the human body may adapt upon contact with the skin.

The carrier may be included in the composition for external application for skin according to the present disclosure in an amount of from about 1% to about 99.99% by weight, preferably from about 90% to about 99.99% by weight based on the total weight of the composition. However, since the ratio varies depending on the formulation as described below in which the composition for external application for skin of the present disclosure is prepared, the specific application site (face, neck, etc.) or the desired amount of application thereof, the ratio should not be construed as limiting the scope of the present disclosure in any aspect.

Examples of the carrier may include alcohol, oil, surfactant, fatty acid, silicone oil, wetting agent, humectant, viscosity modifier, emulsion, stabilizer, UV scattering agent, UV absorber, color developer, fragrance, etc. The alcohol, oil, surfactant, fatty acid, silicone oil, wetting agent, humectant, viscosity modifier, emulsion, stabilizer, UV scattering agent, UV absorber, coloring agent, perfume, etc., are already known in the art, and thus those skilled in the art can select and use an appropriate material/composition.

As an embodiment of the present disclosure, the cosmetic composition according to the present disclosure may contain glycerin, butylene glycol, propylene glycol, polyoxyethylene hydrogenated castor oil, ethanol, triethanolamine, etc., in addition to the phytoplacenta cell culture extract, and a trace amount of preservatives. fragrance, colorant, purified water, etc., as needed, may be included.

The cosmetic composition according to the present disclosure may be prepared in various forms, for example, skin lotions, essences, gels, emulsions, lotions, creams (oil-in-water type, water-in-oil type, multi-phase), solutions, suspensions (anhydrous and water-based), anhydrous products (oil and glycol-based), gels, masks, packs, powders, or capsules with a coating such as gelatin (soft capsules, hard capsules) formulations, etc.

The skin in the present disclosure is a concept that includes not only the face, but also the scalp and the whole body, and as a composition for external application for skin that may be applied to the scalp, there are shampoos, rinse, treatments, hair growth agents, etc., and a body cleanser that may be applied to the whole body may be prepared in various forms for such purposes.

The method for preparing the cosmetic composition containing the phytoplacenta cell culture extract of Taraxacum Coreanum according to the present disclosure is not limited to the above-mentioned preparing method, and those of ordinary skill in the art to which the present disclosure pertains, are also possible to prepare a cosmetic composition containing the phytoplacenta cell culture extract of Taraxacum Coreanum according to the present disclosure.

In particular, the cosmetic composition may be prepared in the form of a general emulsified formulation and a solubilized formulation by using a conventionally known preparing method in addition to the preparing method specifically disclosed in the present disclosure.

When prepared as a cosmetic composition, examples of the cosmetic products in an emulsified form include nutrient lotion, cream, and essence, etc., and examples of the cosmetic products in a solubilized form include a softening cosmetic product. In addition, by containing a dermatologically acceptable medium or base, the cosmetic composition may be prepared in the form of an adjuvant that may be applied topically or systemically, commonly used in the field of dermatology.

In addition, suitable cosmetic formulations may be provided, for example, in the form of solutions, gels, solid or kneaded dry products, emulsions obtained by dispersing an oil phase in an aqueous phase, suspensions, microemulsions, microcapsules, microgranules or ionic (liposomes), nonionic vesicular dispersant, creams, skins, lotions, powders, ointments, sprays or concealers. In addition, the cosmetic formulation may be prepared in the form of a foam or an aerosol composition further containing a compressed propellant.

In addition, the cosmetic composition according to the present disclosure may further contain fatty substances, organic solvents, solubilizers, thickening agents and gelling agents, emollients, antioxidants, suspending agents, stabilizers, foaming agents, fragrances, surfactants, water, ionic or nonionic emulsifiers, fillers, sequestering and chelating agents, preservatives, vitamins, blocking agents, wetting agents, essential oils, dyes, pigments, hydrophilic or lipophilic actives, lipid vesicles or adjuvants commonly used in the field of cosmetology or dermatology, such as any other ingredients conventionally used in cosmetics. Also, the above ingredients may be introduced in an amount generally used in the field of dermatology.

Hereinafter, the present disclosure will be described in more detail through examples. These examples are only for illustrating the present disclosure, and it will be apparent to those of ordinary skill in the art that the scope of the present disclosure is not to be construed as being limited by these examples.

In particular, in the following examples, the efficacy of the Taraxacum Coreanum phytoplacenta cell culture extract was confirmed, and it will be apparent to those skilled in the art that the culture itself but not extracts has an effect.

Advantageous Effects

The phytoplacenta cell culture of Taraxacum Coreanum or an extract thereof according to the present disclosure is non-toxic to skin cells, and has an efficacy of moisturizing, anti-aging, strengthening the skin barrier, improving wrinkles, soothing the skin, protecting the skin from UV rays, and protecting the skin from blue light, etc.

BEST MODE

Hereinafter, the present disclosure will be described in more detail through the following examples. However, these examples are for illustrative purposes only and the scope of the present disclosure is not limited to these examples.

Example 1: Preparation of Composition According to the Present Disclosure

Example 1-1: Surface Disinfection of Plants

For plant cell production according to the present disclosure, the flower bud of Taraxacum Coreanum was carefully peeled off with tweezers to separate the phytoplacenta cells. Thereafter, the phytoplacenta cells were immersed in 70% ethanol for 30 seconds, and sterilized by shaking it in 2% sodium hypochlorite for 5 minutes, and then, was washed with sterile water.

Example 1-2: Induction of Plant Phytoplacenta Cell

Sterilized phytoplacenta cells were cut at once using a sharp knife, and early plant cells were induced by culturing the cells in the dark in a basal MS medium (Murashige and Skoog 1962, Duchefa, Cat. M0221) under growth conditions at 25° C. and 70% humidity wherein 100 mg of myoinositol as plant growth regulators, 0.4 mg of thiamine, 0.1 mg of zeatin, 30 g of sucrose are included in the basal MS medium (based on 1 L). Each medium was adjusted to pH 5.8 with 1N NaOH. Subcultures were performed at two-week intervals.

Example 1-3: Plant Phytoplacenta Cell Culture and Mass Production According to the Present Disclosure The Taraxacum Coreanum phytoplacenta cells cultured through aseptic subculture were then constantly controlled at temperature 25° C., humidity 70%, air supply 0.1 vvm in a liquid medium of the same composition except for agar using a bioreactor, and ware mass-produced by culturing and proliferating at intervals of 14 days.

Example 1-4: Preparation of Plant Phytoplacenta Cell Composition According to the Present Disclosure The cultured Taraxacum Coreanum phytoplacenta cells were harvested, the moisture was sufficiently removed with a clean tissue, and then the obtained cells were dried at 60° C. for 2 days. In order to obtain a composition according to the present disclosure, 20 g of Taraxacum Coreanum phytoplacenta cells were extracted with 10 L of purified water at 60 to 80° C. for 6 to 8 hours under reduced pressure at low temperature, and filtered.

Experimental Example 1: Skin Cell Non-Irritating Effect Confirmation Test

First, in order to find out whether the composition according to the present disclosure of Example 1 was stimulated by toxicity for each treatment concentration in skin cells, an MTT assay for measuring cell viability was performed.

For this, HaCaT cells (keratinocytes) and Detroit cells (fibroblasts) were each dispensed to 96-well plate with DMEM (Dubelcco's Modified Eagle's Medium) containing 10% Fetal Bovine Serum (FBS) and 1% antibiotic-antimycotic and incubated for 24 hours in an incubator under the conditions of 5% $CO_2$ and 37° C. Thereafter, the cells were treated with the composition as a control to which purified water was added and a test substance to be a final concentration of 1, 5, and 10%, and further cultured for 24 hours. Then, 5 mg/mL of a solution of MTT(3-(4,5-dimethyl-2-thiazolyl)-2,5-diphenyl-2H-tetrazolium bromide) was added to each well in an amount of 4 µL, and incubated for 4 hours to allow the reaction. After removing the culture medium, 100 µL of a solution of dimethyl sulfoxide (DMSO) was added to dissolve the cells, and the absorbance was measured at 540 nm.

TABLE 1

| Sample | Treatment concentration (%) | Viability of HaCaT cell (%) | Viability of Detroit cell (%) |
|---|---|---|---|
| Control | — | 100.00 | 100.00 |
| Experimental group | 1 | 101.26 | 98.01 |
|  | 5 | 100.46 | 96.93 |
|  | 10 | 97.96 | 96.73 |

As a result, when the composition according to the present disclosure was treated by concentration of 1 to 10%, all cell viability compared to the control group was 95% or more, which did not cause intradermal toxicity. Accordingly, it was confirmed that the "Taraxacum Coreanum phytoplacenta cell culture extract" has a low possibility of causing irritation to skin cells and is harmless to skin cells.

Experimental Example 2: Antioxidant Effect Confirmation Test from DPPH Radical Scavenging Ability In order to examine the antioxidant effect of the composition according to the present disclosure due to inhibition of 1,1-diphenyl-2-picrylhydrazyl (DPPH) free radical generation, DPPH assay was performed.

For this, 500 µL of a 0.1 mM DPPH solution and 100 µL of the composition as a control and a test substance were added to 400 µL of ethanol. After mixing each sample, it was reacted for 30 minutes in the dark at room temperature, and the absorbance was measured at 517 nm.

TABLE 2

| Sample | Treatment concentration (%) | DPPH radical scavenging ability (%) |
|---|---|---|
| Control | — | 0.00 |
| Experimental group | 1 | 3.61 |
|  | 5 | 11.68 |
|  | 10 | 23.84 |

As a result, it was confirmed that when the composition according to the present disclosure was treated by concentration each, the DPPH radical scavenging ability was increased compared to the control group, thereby confirming that the "Taraxacum Coreanum phytoplacenta cell culture extract" had an antioxidant effect.

Experimental Example 3: Antioxidant Effect Confirmation Test from $H_2O_2$ Oxidative Toxicity In order to examine the antioxidant effect from the $H_2O_2$ oxidative toxicity of the composition according to the present disclosure, the change in cell viability by $H_2O_2$ was investigated.

To this end, HaCaT cells were dispensed to a 48-well plate, and then cultured for 24 hours in cell culture conditions. Thereafter, 1 mM $H_2O_2$ was irradiated, and the cells were treated with the composition as a control and a test substance, and further cultured for 12 to 16 hours. In this case, 2 mM of N-acetylcy-L-steine (NAC) was used as a positive control. Thereafter, cell viability was measured using the MTT assay to confirm whether the skin cells were protected from damage caused by the induction of $H_2O_2$ oxidative toxicity.

TABLE 3

| Sample | Treatment concentration (%) | $H_2O_2$ | Viability of HaCaT cell (%) |
|---|---|---|---|
| Control | — | − | 100.00 |
| Control | — | + | 60.33 |
| Positive control | — | + | 88.8 |
| Experimental group | 1 | + | 66.56 |
|  | 5 | + | 76.73 |
|  | 10 | + | 79.46 |

As a result, as cell death by $H_2O_2$ treatment was inhibited in cells treated with the composition according to the present disclosure by concentration each compared to the control (+$H_2O_2$), it was confirmed that the "Taraxacum Coreanum phytoplacenta cell culture extract" had an antioxidant effect from $H_2O_2$ oxidative toxicity.

Experimental Example 4: Wrinkle Improvement Effect Confirmation Test According to Increase in PIP Production In order to examine the wrinkle improvement effect of the composition according to the present disclosure, the biosynthesis amount of procollagen (Procollagen Type I C-Peptide, PIP), which is a precursor of collagen synthesis, was measured.

To this end, Detroit551 cells were dispensed to a 48-well plate, and then cultured for 24 hours in cell culture conditions. After that, the cells were treated with the composition as a control and a test substance, and further cultured for 48 hours. Then, a portion of 20 μL of the diluted supernatant of the culture medium was taken, and it was placed in an antibody-coated microtiter plate together with 20 μL of a PIP standard in a PIP EIA Kit (Takara, Cat. MK101), and 100 μL of a peroxidase-labeled antibody solution was also added to each well and reacted at 37° C. for 3 hours. After removing the medium and washing 4 times with 200 μL of PBS, 100 μL of a substrate solution was added to each well and reacted at room temperature for 15 minutes under light blocking. After that, a 100 μL of a substrate solution (1N $H_2SO_4$) was added, and the absorbance at 450 nm was measured.

TABLE 4

| Sample | Treatment concentration (%) | Ability of synthesizing PIP (%) |
|---|---|---|
| Control | — | 100.00 |
| Positive control | — | 122.60 |
| Experimental group | 1 | 109.5 |
|  | 5 | 114.1 |
|  | 10 | 119.1 |

As a result, as the amount of PIP increased in the cells treated with the composition according to the present disclosure by concentration each compared to the control, it was confirmed that the "Taraxacum Coreanum phytoplacenta cell culture extract" was effective in anti-wrinkle.

Experimental Example 5: Moisturizing and Skin Barrier Improvement Effect Confirmation Test According to Increase in Expression of AQP3 and FLG In order to examine the moisturizing and skin barrier improvement efficacy of the composition according to the present disclosure, changes in the expression levels of AQP3 (Aquaporin), a moisture/glycerol transporter, and FLG (Filaggrin), known as a natural moisturizing factor, were investigated.

HaCaT cells were dispensed to a 96-well plate, and then cultured for 24 hours in cell culture conditions. After that, the cells were treated with the composition as a control and a test substance, and further cultured for 24 hours. Real-time PCR was performed to confirm the gene level of AQP3 and FLG, and the test sequence is as follows.

For RNA isolation and cDNA synthesis, SuperPrepm cell lysis & RT Kit for qPCR (TOYOBO, Cat. SCQ-101) were used. The cells from which the medium was removed were washed once with PBS, and 50 μL of a cell lysis mixture was added and reacted for 5 minutes, followed by addition of a stop solution. 8 μL of the previously extracted lysate was added to 32 μL of the RT reaction mixture, and cDNA was synthesized using PCR at 37° C. for 15 minutes, 50° C. for 5 minutes, and 95° C. for 5 minutes. For comparative analysis of gene expression, the cDNA synthesized above was used as a template, and real-time PCR analysis was performed using Thunderbird™ SYBR qPCR Mix (TOYOBO, Cat. QPS-201). The primer used in the experiment was Qiagen's QuantiTect primer assays (GAPDH; Cat. QT01192646, AQP3; Cat. QT00212996, FLG; Cat. QT02448138), and the AQP3 and FLG mRNA expression levels of the samples were quantified by GADPH. Real-time qPCR conditions were first performed at 95° C. for 1 minute, followed by performing a total of 40 cycles at 94° C. for 15 seconds, 60° C. for 30 seconds, and 72° C. for 30 seconds per cycle.

TABLE 5

| Sample | Treatment concentration (%) | Relative Expression level (Fold) | |
|---|---|---|---|
|  |  | AQP3 | FLG |
| Control | — | 1.00 | 1.00 |
| Experimental group | 1 | 1.49 | 1.83 |
|  | 5 | 2.37 | 1.77 |
|  | 10 | 2.11 | 1.66 |

As a result, as the mRNA expression levels of AQP3 and FLG increased in cells treated with the composition according to the present disclosure by concentration each compared to the control group, it was confirmed that "Taraxacum Coreanum phytoplacenta cell culture extract" was effective in moisturizing and an improvement of the skin barrier.

Experimental Example 6: Anti-Inflammatory Effect Confirmation Test According to COX-2 Expression Reduction In order to examine the anti-inflammatory effect of the composition according to the present disclosure, a change in the expression level of COX-2 (Cyclooxygenase-2) involved in the inflammatory response was investigated.

To this end, HaCaT cells were dispensed to a 96-well plate, and then cultured for 24 hours in cell culture conditions. Thereafter, an inflammatory response was induced through UVB irradiation, the cells were treated with the composition as a control and a test substance, and further cultured for 4 hours. Real-time PCR was performed to confirm the gene level of COX-2, and the test sequence is as follows.

For RNA isolation and cDNA synthesis, SuperPrep™ cell lysis & RT Kit for qPCR (TOYOBO, Cat. SCQ-101) were used. The cells from which the medium was removed were washed once with PBS, and 50 μL of a cell lysis mixture was added and reacted for 5 minutes, followed by addition of a stop solution. 8 μL of the previously extracted lysate was added to 32 μL of the RT reaction mixture, and cDNA was synthesized using PCR at 37° C. for 15 minutes, 50° C. for 5 minutes, and 95° C. for 5 minutes. For comparative analysis of gene expression, the cDNA synthesized above was used as a template, and real-time PCR analysis was performed using Thunderbird™ SYBR qPCR Mix (TOYOBO, Cat. QPS-201). The primer used in the experiment was Qiagen's QuantiTect primer assays (GAPDH; Cat. QT01192646, COX-2; Cat. QT00040586), and the COX-2 mRNA expression levels of the samples were quantified by GADPH. Real-time qPCR conditions were first performed at 95° C. for 1 minute, followed by performing a total of 40 cycles at 94° C. for 15 seconds, 60° C. for 30 seconds, and 72° C. for 30 seconds per cycle.

TABLE 6

| Sample | Treatment concentration (%) | UVB | Relative Expression level of COX-2(Fold) |
|---|---|---|---|
| Control | — | − | 0.129 |
| Control | — | + | 1.00 |
| Experimental group | 1 | + | 0.88 |
|  | 5 | + | 0.67 |
|  | 10 | + | 0.54 |

As a result, as the mRNA expression level of COX-2 decreased in the cells treated with the composition according to the present disclosure by concentration each compared to the control (UVB treatment), it was confirmed that the "Taraxacum Coreanum phytoplacenta cell culture extract" had an anti-inflammatory effect.

Experimental Example 7: Skin Cell Protective Effect Confirmation Test from UV Stimulation In order to examine the skin cell protective effect of the composition according to the present disclosure from UV stimulation, the change in cell viability was investigated.

To this end, HaCaT cells were dispensed to a 96-well plate, and then cultured for 24 hours in cell culture conditions. After that, UV was irradiated, the cells were treated with the composition as a control and a test substance, and further cultured for 24 hours. Then, cell viability was measured by using the MTT assay to confirm whether the UV-induced damage to skin cells was protected.

TABLE 7

| Sample | Treatment concentration (%) | UVB | Viability of HaCaT cell (%) |
|---|---|---|---|
| Control | — | − | 100.00 |
| Control | — | + | 40.46 |
| Experimental group | 1 | + | 49.60 |
|  | 5 | + | 54.06 |
|  | 10 | + | 60.46 |

As a result, as cell death by UVB treatment was inhibited in cells treated with the composition according to the present disclosure by concentration each compared to the control (+UVB), it was confirmed that "Taraxacum Coreanum phytoplacenta cell culture extract" had a cytoprotective effect from UV rays.

Experimental Example 8: Skin Cell Protective Effect Confirmation Test from Blue Light Induction In order to examine the skin cell protective effect of the composition according to the present disclosure from blue light stimulation, the change in cell viability was investigated.

To this end, HaCaT cells were dispensed to a 96-well plate, and then cultured for 24 hours in cell culture conditions. After that, the cells were treated with the composition as the control and test substance, and after 2 hours, the cells were irradiated with blue light for 6 hours using Topview 5450 VRI SMD LED (ITSWELL, Cat. IWS-L5056-VRI-K3), and then the cells were further cultured for 24 hours. Then, cell viability was measured by using the MTT assay to confirm whether the blue light-induced damage to skin cells was protected.

TABLE 8

| Sample | Treatment concentration (%) | Blue light | Viability of HaCaT cell (%) |
|---|---|---|---|
| Control | — | − | 100.00 |
| Control | — | + | 74.1 |
| Experimental group | 1 | + | 82.01 |
|  | 5 | + | 88.43 |
|  | 10 | + | 89.62 |

As a result, as cell death by blue light treatment was inhibited in the cells treated with the composition according to the present disclosure by concentration each compared to the control (+blue light), it was confirmed that "Taraxacum Coreanum phytoplacenta cell culture extract" had a cytoprotective effect from blue light.

Experimental Example 9: Anti-Aging Effect Confirmation Test According to TERT Expression Increase In order to examine the anti-aging efficacy of the composition according to the present disclosure, a change in the expression level of telomerase reverse transcriptase (TERT), which is known as an enzyme extending the length of telomeres at the ends of DNA strands, was investigated.

A change in the expression level of telomerase reverse transcriptase (TERT), which is known as an enzyme that extends the length of telomeres at the ends of DNA strands, was investigated.

HaCaT cells were dispensed to a 96-well plate, and then cultured for 24 hours in cell culture conditions. After that, the cells were treated with the composition as a control and a test substance, and further cultured for 24 hours. Real-time PCR was performed to confirm the gene level of TERT, and the test sequence is as follows.

For RNA isolation and cDNA synthesis, SuperPrep™ cell lysis & RT Kit for qPCR (TOYOBO, Cat. SCQ-101) were used. The cells from which the medium was removed were washed once with PBS, and 50 μL of a cell lysis mixture was added and reacted for 5 minutes, followed by addition of a stop solution. 8 μL of the previously extracted lysate was added to 32 μL of the RT reaction mixture, and cDNA was synthesized using PCR at 37° C. for 15 minutes, 50° C. for 5 minutes, and 95° C. for 5 minutes. For comparative analysis of gene expression, the cDNA synthesized above was used as a template, and real-time PCR analysis was performed using Thunderbird™ SYBR qPCR Mix (TOYOBO, Cat. QPS-201). The primer used in the experiment was Qiagen's QuantiTect primer assays (GAPDH; Cat. QT01192646, TERT; Cat. QT00073409), and the TERT mRNA expression levels of the samples were quantified by GADPH. Real-time qPCR conditions were first performed at 95° C. for 1 minute, followed by performing a total of 40 cycles at 94° C. for 15 seconds, 60° C. for 30 seconds, and 72° C. for 30 seconds per cycle.

TABLE 9

| Sample | Treatment concentration (%) | Relative Expression level of TERT(Fold) |
|---|---|---|
| Control | — | 1 |
| Experimental group | 1 | 1.38 |
|  | 5 | 1.67 |
|  | 10 | 1.81 |

As a result, as the mRNA expression level of TERT increased in the cells treated with the composition according to the present disclosure by concentration each compared to the control, it was confirmed that the "Taraxacum Coreanum phytoplacenta cell culture extract" was effective in anti-aging.

Experimental Example 10: Anti-Stress Effect Confirmation Test According to LEA Expression Increase In order to examine the anti-stress effect of the composition according to the present disclosure, the expression change of LEA (Late embryogenesis abundant), which is known to protect cell damage against stress, was investigated.

To this end, HaCaT cells were dispensed to 6-well plate, and then cultured for 24 hours in conditions for culturing cell. After that, the cells were treated with the composition as a control and a test substance, and then the cells were further cultured for 24 hours, and an In-Cell ELISA Colorimetric Detection kit (Invitrogen, Cat No. 62200) was used to measure the LEA protein expression level. The finished culture medium was removed and the cells were fixed by incubating at room temperature for 15 minutes with 100 µL fixing solution. After that, it was washed with PBS, and 100 µL of a permeabilization solution was added and reacted at room temperature for 15 minutes. After that, it was washed with PBS, and 100 µL of quenching solution was added and reacted at room temperature for 20 minutes. After that, it was washed with PBS, and 100 µL of a blocking solution was added and reacted at room temperature for 30 minutes. After removing the solution, 50 µL of LEA primary antibody was added and reacted at 4° C. for 24 hours. After removing the antibody, it was washed with PBS, and 50 µL of HRP-conjugated secondary antibody was added and reacted for 1 hour. After removing the antibody and washing with PBS, 100 µL of a TMB substrate solution was added and reacted at room temperature for 15 minutes while blocking the light. Then, 100 µL of a stop solution (1N $H_2SO_4$) was added, and the absorbance at 450 nm was measured.

TABLE 10

| Sample | Treatment concentration (%) | UVB | Ability for synthesizing LEA protein (%) |
|---|---|---|---|
| Control | — | − | 68.57 |
| Control | — | + | 100.00 |
| Experimental group | 1 | + | 103.21 |
|  | 5 | + | 108.85 |
|  | 10 | + | 111.95 |

As a result, as the expression level of LEA was increased by UVB treatment in cells treated with the composition according to the present disclosure by concentration each compared to the control (+UVB), it was confirmed that "Taraxacum Coreanum phytoplacenta cell culture extract" had a stress relieving effect by protecting cell damage.

Experimental Example 11: (In Vivo) Fine Dust Blocking Effect Confirmation Test

The fine dust blocking effect of the essence formulation to which 1% of the composition according to the present disclosure was applied was investigated.

First, the essence formulation was prepared, in the case of the experimental group, with 1 part by weight of a Taraxacum Coreanum phytoplacenta cell culture extract, 1 part by weight of betaine, 0.5 parts by weight of dipalmitoylhydroxyproline, 0.3 parts by weight of 1,2 hexanediol, 0.2 parts by weight of carbomer, 0.1 parts by weight of propylene glycol, 0.05 parts by weight of sorbitol, 0.02 parts by weight of sodium hydroxide, and 100 parts by weight of the remaining purified water, and a control of essence formulation is that 1 part by weight of a Taraxacum Coreanum phytoplacenta cell culture extract which is a composition according to the present disclosure was excluded from the experimental group.

For the test, a square (2 cm×2 cm) was partitioned on the forearms of 20 subjects, the product was applied in an amount of 50 µL each, and the test site was exposed to a fine dust floating chamber equipped with a propeller for 1 minute. Substitute fine dust was carbon black (Korea Carbon Black Co., Ltd., Corax N220, particle size: 20 to 25 nm), and 1 g was suspended in the chamber. Measurements were carried out before adsorption of alternative fine dust and after adsorption of alternative fine dust. For photography, a digital camera (Canon, EOS70D) was used to take a picture of the forearm. The photographed images were analyzed using the image analysis program (Image-Pro® plus) to designate the Area of Interest (AO') of the test site, and then analyze the difference in pixel values before and after adsorption of fine dust. The unit is an Arbitrary Unit (A.U.).

TABLE 11

| Sample | Treatment concentration (%) | Fine dust | Pixel change level |
|---|---|---|---|
| Control 1 | — | − | 0.00 |
| Control 2 | — | + | 20.01 |
| Experimental group | 1 | + | 14.65 |

Improvement (%) of the effect of preventing the adsorption of the substituting fine dust in the experimental group compared to the control group=[1−(the change level of the substituting fine dust pixel in the experimental group)/(the change level of the substituting fine dust pixel in the control group 2)]*100

As a result, the experimental group to which the composition according to the present disclosure was applied showed a 26.79% improvement in the prevention of fine dust adsorption compared to the control group 2. Therefore, "Taraxacum Coreanum phytoplacenta cell culture extract" is judged to be a product that helps preventing the adsorption of fine dust.

Experimental Example 12: (In Vivo) Skin Soothing Effect Confirmation Test

The skin soothing effect according to the skin temperature reduction rate of the essence formulation to which 1% of the composition according to the present disclosure was applied, was investigated.

For this purpose, a square (2 cm×2 cm) was partitioned on the forearms of 25 subjects, and the product was applied in an amount of 50 µL each, and then exposed to direct sunlight for 20 minutes before the test. Measurement was performed using a computerized infrared thermographic imaging sensor (DITI) to measure body heat at intervals of 0 minute (before sample application), 5 minutes (after sample application), and 10 minutes (after application of sample), and the temperature reduction rate was calculated.

TABLE 12

| Sample | Treatment concentration (%) | Heat reduction rate (%) | | |
|---|---|---|---|---|
| | | After 0 minute | After 5 minutes | After 20 minutes |
| Control | — | 7.1 | 3.1 | 0.9 |
| Experimental group | 1 | 7.3 | 5.5 | 3.8 |

As a result, it was confirmed that the continuous heat reduction rate was maintained even after 20 minutes compared to the control group in the experimental group to which the composition according to the present disclosure was applied. Therefore, it was confirmed that "Taraxacum Coreanum phytoplacenta cell culture extract" had a skin soothing effect.

As described above, a specific part of the content of the present disclosure has been described in detail, and for one skilled in the art, it will be obvious that this specific technology is only a preferred embodiment, and the scope of the present disclosure is not limited thereby. Therefore, it will be said that the substantial scope of the present disclosure is defined by the appended claims and their equivalents.

The invention claimed is:

1. A method for preparing a composition containing a phytoplacenta cell culture of Taraxacum Coreanum or an extract of the phytoplacenta cell culture, the method comprising the steps of:
   (a) separating and culturing phytoplacenta cells from the phytoplacenta tissue in an ovary of Taraxacum Coreanum plant; and
   (b) preparing a composition containing the phytoplacenta cell culture obtained in the step (a) or an extract of the phytoplacenta cell culture obtained in the step (a);
   wherein step (a) includes culturing the phytoplacenta cells in the dark; and
   wherein the extract of the phytoplacenta cell culture in the step (b) is obtained by extracting the phytoplacenta cell culture of Taraxacum Coreanum obtained in the step (a) at 60° C. to 80° C. for 6 to 8 hours.

2. The method of claim 1, wherein step (b) includes drying, pulverizing, and mixing the phyplacenta cell culture of Taraxacum Coreanum plant obtained in the step (a) with purified water.

3. The method of claim 2, wherein step (b) after mixing the phytoplacenta cell culture of Taraxacum Coreanum plant performing ultrasonic extraction or hot water extraction.

4. A cosmetic composition comprising a phytoplacenta cell culture of Taraxacum Coreanum or the extract of the phytoplacenta cell culture and a carrier acceptable in cosmetic formulation, wherein the phytoplacenta cell culture of Taraxacum Coreanum or the extract of the phytoplacenta cell culture is present in an amount ranging from 0.1 to 10% by weight, based on the total weight of the composition.

5. A cosmetic composition according to claim 4 comprising an effective amount of the phytoplacenta cell culture or the extract of the phytoplacenta cell culture to moisturize skin.

6. A cosmetic composition according to claim 4 comprising an effective amount of the phytoplacenta cell culture or the extract of the phytoplacenta cell culture to improve a skin barrier.

7. A cosmetic composition according to claim 4 comprising an effective amount of the phytoplacenta cell culture or the extract of the phytoplacenta cell culture to protect skin from ultraviolet rays.

8. A cosmetic composition according to claim 4 comprising an effective amount of the phytoplacenta cell culture or the extract of the phytoplacenta cell culture to protect skin from blue light.

9. A cosmetic composition according to claim 4 comprising an effective amount of the phytoplacenta cell culture or the extract of the phytoplacenta cell culture to prevent or alleviate skin stress.

10. A cosmetic composition according to claim 4 comprising an effective amount of the phytoplacenta cell culture or the extract of the phytoplacenta cell culture to protect skin from fine dust.

11. A cosmetic composition according to claim 4 comprising an effective amount of the phytoplacenta cell culture or the extract of the phytoplacenta cell culture to soothe the skin.

12. A cosmetic composition according to claim 4 comprising an effective amount of the phytoplacenta cell culture or the extract of the phytoplacenta cell culture to improve or prevent skin wrinkles.

13. The cosmetic composition according to claim 4, wherein the phytoplacenta cell culture of Taraxacum Coreanum or the extract of the phytoplacenta cell culture is present in an amount ranging from 1 to 10% by weight, based on the total weight of the composition.

14. The method of claim 1, wherein the extract of the phytoplacenta cell culture in the step (b) is obtained by extracting the phytoplacenta cell culture of Taraxacum Coreanum obtained in the step (a) at 60° C. to 80° C. for 6 to 8 hours at a pressure ranging from 0.03 to 0.3 MPa.

15. The method of claim 1, wherein the extract of the phytoplacenta cell culture in the step (b) is obtained by extracting the phytoplacenta cell culture of Taraxacum Coreanum obtained in the step (a) at 60° C. to 80° C. for 6 to 8 hours at a pressure ranging from 0.05 to 0.1 MPa.

16. A cosmetic composition comprising a phytoplacenta cell culture of Taraxacum Coreanum or the extract of the phytoplacenta cell culture and a carrier acceptable in cosmetic formulation, wherein the Phytoplacenta cell culture of Taraxacum Coreanum or the extract of the phytoplacenta cell culture is present in an amount ranging from 0.1 to 10% by weight, based on the total weight of the composition,
   wherein the phytoplacenta cell culture of Taraxacum Coreanum or the extract of the phytoplacenta cell culture is prepared by the method of claim 12.

17. The cosmetic composition according to claim 16, wherein the Phytoplacenta cell culture of Taraxacum Coreanum or the extract of the phytoplacenta cell culture is present in an amount ranging from 1 to 10% by weight, based on the total weight of the composition.

* * * * *